United States Patent [19]

Schönwälder

[11] Patent Number: 5,223,642
[45] Date of Patent: Jun. 29, 1993

[54] PROCESS FOR THE PREPARATION OF ETHER CARBOXYLIC ACIDS FROM CARBOHYDRATES AND DERIVATIVES THEREOF AND THEIR USE

[75] Inventor: Karl-Heinz Schönwälder, Kelkheim/Taunus, Fed. Rep. of Germany

[73] Assignee: Hoechst Aktiengesellschaft, Frankfurt am Main, Fed. Rep. of Germany

[21] Appl. No.: 835,987

[22] PCT Filed: Aug. 18, 1990

[86] PCT No.: PCT/EP90/01364
§ 371 Date: Mar. 30, 1992
§ 102(e) Date: Mar. 30, 1992

[87] PCT Pub. No.: WO91/02712
PCT Pub. Date: Mar. 7, 1991

[30] Foreign Application Priority Data

Aug. 26, 1989 [DE] Fed. Rep. of Germany ....... 3928310

[51] Int. Cl.$^5$ ............................................. C07C 67/00
[52] U.S. Cl. ...................................... 562/524; 562/523; 562/538; 562/421; 252/89.1; 252/142
[58] Field of Search ............... 562/523, 524, 538, 421; 252/89.1, 142

[56] References Cited

U.S. PATENT DOCUMENTS

| 3,799,977 | 3/1974 | Rutledge | 260/531 R |
|---|---|---|---|
| 4,082,788 | 4/1978 | Mims | 562/524 X |
| 4,214,101 | 7/1990 | Miya et al. | 562/421 |
| 4,952,721 | 8/1990 | Fjare | 562/524 X |

FOREIGN PATENT DOCUMENTS 0302007 2/1989 European Pat. Off. .
2391185 12/1978 France .

OTHER PUBLICATIONS

Sanyo Kasei Kogyo K.K., *Pat. Abs. of Japan 6:* No. 131, Abstract of JP 57-58642 (Apr. 8, 1992).

Primary Examiner—Arthur C. Prescott

[57] ABSTRACT

A process for the preparation of ether carboxylic acids by ethoxylation of carbohydrates followed by catalytic oxidation and the use of the products in detergents or cleaning agents.

16 Claims, No Drawings

PROCESS FOR THE PREPARATION OF ETHER CARBOXYLIC ACIDS FROM CARBOHYDRATES AND DERIVATIVES THEREOF AND THEIR USE

DESCRIPTION

The present invention relates to a process for the preparation of ether carboxylic acids by ethoxylation of carbohydrates, followed by catalytic oxidation, and to the use of the products obtained.

Owing to their eutrophying effect in lakes and rivers, the use of phosphates in detergents and cleaning agents has become restricted by law and in some cases even prohibited in a number of countries. As a result, a large number of substitutes for phosphates, in particular for sodium tripolyphosphate, have been developed and proposed in the meantime as builder. However, the desirable properties of sodium tripolyphosphate in its application as a detergent have hitherto not been achieved entirely by any single substance. Rather, only combinations of builders are capable of achieving in a first approximation the effect of phosphates. Only a relatively small number of phosphate substitutes, or rather partial substitutes, are fully satisfactory with respect to their ecological properties. Although they do not promote eutrophication of lakes and rivers, they have nevertheless in some cases properties which must be regarded as questionable in their effect on the environment, such as remobilization of heavy metals from sediments of the lakes and rivers or insufficient biological degradability; therefore, their effect on the environment is uncertain, even if these substances do not immediately have to be considered toxic according to current knowledge. Accordingly, the search for effective builders for detergents which can be considered safe with respect to their ecological effect continues.

In JP-A2-58/117,284 so-called viscosity-reducing agents of coal sludges are disclosed, which can be prepared by reaction of polyhydric alcohols, which also include carbohydrates, with alkylene oxides to give polyether compounds, followed, if desired, by conversion of the terminal hydroxyl groups into carboxyl groups; however, more detailed information on the synthesis of these products is not given.

Ethoxylation of carbohydrates has been known for quite a long time. Thus, for example, W. Gerhardt, J. f. prakt. Chem., 4th series, 29, 300 (1965) has described ethoxylation of saccharose; JP-A2-58/117,284 also mentions further carbohydrates. However, economical processes for the preparation of oxidized ethoxylates of carbohydrates and the use of such products as builders are hitherto not known.

Accordingly, the object was to develop biologically degradable phosphate substitutes and an economical and industrially feasible method of preparation.

Surprisingly, it has now been found that biologically degradable phosphate substitutes having good lime-binding power are obtained by ethoxylating carbohydrates, followed, if desired, by alkoxylation by means of a higher alkylene oxide, and converting the terminal primary hydroxyl groups into carboxyl groups by catalytic oxidation.

Accordingly, the invention relates to a process for the preparation of ether carboxylic acids by alkoxylation of carbohydrates and derivatives thereof, followed by oxidation, which process comprises either ethoxylating the carbohydrates or derivatives thereof directly in the usual manner or first alkoxylating them using a higher alkylene oxide and then ethoxylating them and oxidizing the aqueous solution thus obtained without any further treatment in a pH range in which the carbohydrates and carboxylic acids derived therefrom are stable, using oxygen as the oxidizing agent in the presence of a catalyst containing at least one platinum metal.

The invention furthermore also relates to the use of these ether carboxylic acids in particular as additive (builder) in detergents or cleaning agents.

The ether carboxylic acids prepared by the process according to the invention are suitable in particular as builders in detergents and cleaning agents, due to their surprisingly high lime-binding power.

Suitable starting materials are virtually any carbohydrates having at least one alkoxylatable hydroxyl group and one alcohol group which can be oxidized to a carboxyl group, such as glucose, galactose, maltose, lactose, fructose, $\beta$-cyclodextrin, in particular saccharose. Examples of suitable derivatives are $\alpha$-methylD-glucoside, sorbitol, mannitol, 2-desoxy-D-ribose and D-glucosamine.

Ethoxylation and alkoxylation are carried out in the usual manner, i.e. in general in aqueous solution under the action of basic catalysts at temperatures of between 50° and 150° C., preferably in a pressure range from atmospheric pressure to 15 bar. The solution containing the compounds having the terminal hydroxyethyl groups is subjected to catalytic oxidation, preferably after dilution to a water content of 70-90% by weight, resulting in the formation of the ether carboxylic acids. Advantageously, at least 50%, preferably at least 75%, and in particular about 100%, of the hydroxyl groups of the carbohydrates and of the derivatives should be alkoxylated Suitable higher alkylene oxides are butylene oxide, styrene oxide and in particular propylene oxide. These can be used, for example, in an amount of up to 3 mol, advantageously of at least 0.1 mol. Naturally, the percentage of higher alkylene oxides chosen is advantageously such that biological degradability is ensured.

The ethylene oxide is advantageously used in an amount of at least 1 mol, for example of up to 10 mol and preferably of up to 5 mol. All mole data given refer to moles of hydroxyl groups present in the carbohydrate or the derivative thereof. If these are first reacted with an alkylene oxide other than ethylene oxide, the total amount of the converted alkylene oxide, i.e. including ethylene oxide, is advantageously not more than 5 mol.

Suitable catalysts are those containing platinum metals, i.e. osmium, iridium, rhodium, ruthenium, palladium and/or platinum. Preference is given to catalysts containing a combination of palladium and platinum and in particular only platinum. Preferably, the platinum metals have been deposited on a support, such as $Al_2O_3$ or $SiO_2$, in particular on activated carbon. The metal content of the catalyst is in general 1 to 15, preferably 5 to 10, % by weight.

Occasionally, it may be advantageous, in particular when the starting materials used are carbohydrate derivatives having poorer water solubility, to add a solubilizing agent which is inert under the reaction conditions, preferably in a concentration of 10 to 75% by weight, in particular 30 to 50% by weight, relative to the amount of water and solubilizing agent. Suitable solubilizing agents are in particular those which have low volatility upon passage of oxygen through the aqueous solution, thus substantially avoiding any risk of explosion in the vapor space; on the other hand, it is desirable that the solubilizing agent can be easily separated off after oxidation, for example by distillation. Examples of suitable solubilizing agents are glycol ethers without free OH groups, such as those of the formula $R^1O\ (CHRCH_2O)_nR^2$, in which n is a number from 1 to 4, R is H or $CH_3$ and $R^1$ and $R^2$ are each, independently of one another, $C_1$–$C_4$-alkyl. Dimethyl ethers, diethyl ethers and methyl ethyl ethers of the general formula mentioned and having boiling points in the range from 100° to about 250° C., for example triethylene glycol dimethyl ether and preferably diethylene glycol dimethyl ether, are particularly suitable.

The preferred oxidizing agent is pure oxygen. However, it is also possible to use mixtures of oxygen with gases which are inert under the reaction conditions, for example mixtures of oxygen with inert gases. Air itself is of course also suitable.

As a rule, the oxidation is carried out at a total pressure of 0.5 to 100 bar. The reaction rate increases noticeably with increasing oxygen partial pressure; however, the advantage of the higher reaction rate may be overcompensated with respect to economy by the more complicated apparatus necessary when higher pressure is applied. A pressure range from atmospheric pressure to 10 bar (absolute) is preferred, it being particularly easy to operate at atmospheric pressure.

As a rule, oxidation is carried out at a temperature from 5° to 80° C., preferably from 10° to 60° C., in particular from 20° to 40° C. Since many carbohydrates and carboxylic acids derived therefrom have low stability in the acidic range, oxidation is advantageously carried out in an approximately neutral to weakly alkaline medium, i.e. in a pH range from 5 to 9, preferably from 6 to 8.5 and in particular from 7 to 8. The carboxylic acids formed during oxidation are advantageously trapped, for example by suitable buffer substances, or advantageously by addition of aqueous bases, for example alkali metal hydroxide or alkaline earth metal hydroxide solutions, which are advantageously metered in in such a way that the pH of the reaction system remains in the range from 6 to 9 during oxidation. In the case of complete neutralization, the oxidation products are obtained in the form of salts.

The process according to the invention can be carried out in any apparatus which is suitable for carrying out reactions in liquid phase with or without application of superatmospheric pressure. Examples of these are carrying out the reaction in a stirred reactor or in a bubble column containing suspended catalyst. However, oxidation can also be carried out over a solid bed containing granular catalyst in a trickle phase reactor.

The required reaction time is advantageously determined by removing samples of the reaction solution at certain intervals and analyzing them. For example, the yield of the reaction products can be continuously determined in a simple manner by analyzing a sample by means of high-pressure liquid chromatography by comparison with standard solution. It is recommended to optimize the reaction time, since an unnecessarily prolonged introduction of oxygen may lead to overoxidations and thus, for example, to decarboxylations and to reduction in the yield of the desired reaction products.

The reaction mixture can be worked up by customary methods. For example, first the water and any solubilizing agent present are removed by distillation. Purification, for example by chromatography, crystallization or precipitation, is then carried out. It is also possible to separate off the product from the solution obtained during oxidation by passing the solution through basic ion exchangers in the $OH^-$ form. However, it has in general proven advantageous to subject the solution obtained in the course of the reaction to spray-drying.

The lime-binding power of the ether carboxylic acids can be determined by conventional analytical methods, for example by turbidimetric titration or potentiometric titration by means of an ion-specific electrode.

The ether carboxylic acids obtainable according to the invention are suitable in particular as builder in detergents or cleaning agents. In addition, they can also be used as food additive, as crosslinking agent in paint preparations, and the like.

The examples which follow illustrate the invention.

EXAMPLE 1

Preparation 333 g of ethylene oxide were added to 111 g of sucrose and 2.75 g of KOH in 450 ml of water in a 2 l stirred autoclave in such a manner that the temperature was between 85° and 100° C. and the pressure was up to 4 bar. After a reaction time of 2 hours, the solution was cooled to room temperature and made up with water to a total volume of 4 l. After addition of 20 9 of a commercially available catalyst (5% of platinum on activated carbon), this solution was gassed at 50° C. in an externally heated upright glass tube (100 mm in diameter, 800 mm in length) from below through a glass frit with 100 NL/h of oxygen. The pH was maintained at 7 to 7.5 by continuous addition of 30% aqueous sodium hydroxide solution. The oxidation time was 6 h. Spray-drying of the reaction product gave 390 g of a colorless powder having a lime-binding power of 279 mg of $CaCO_3$ per g of substance (determined at room temperature).

EXAMPLE 2

Preparation

Analogously to Example 1, 110 g of sorbitol were ethoxylated with 470 g of ethylene oxide and 4 g of KOH in 950 ml of water and then, after addition of 4.27 l of water and 290 g of catalyst, oxidized. The spray-dried product (484 g) had a lime-binding power of 373 mg of $CaCO_3$/g of substance.

EXAMPLE 3

Preparation

Analogously to Example 1, pentaerythritol and α-methylglucoside were ethoxylated and oxidized and, after workup, tested for their lime-binding power. The product obtained from pentaerythritol had a lime-binding power of 343 mg of $CaCO_3$/g of substance and that obtained from α-methylglucoside a lime-binding power of 327 mg of $CaCO_3$/g of substance.

EXAMPLE 4

Preparation

The superiority of the product obtained according to the invention as builder can be seen in the test results of detergent formulations in which only the saccharose tricarboxylic acid obtained according to German Offenlegungsschrift 3,535,720 was replaced by the product according to the invention of Example 1. The washing test of these detergents was carried out in accordance with the approved technical rules, following DIN 44983:

The washing power (difference in reflectance) was determined photometrically by measuring the reflectance (colorimeter RFC 3 from Zeiss) of two WFK and EMPA test soiled fabrics at a wavelength of 460 nm (WFK=Waschereiforschungsinstitut Krefeld (Laundry Research Institute Krefeld); EMPA=*(Swiss Material Testing Institute, Switzerland)). In this test, the "difference method" according to the equation:

$$\% R = \% R_g - \% R_u \text{ was used.}$$

In this equation
R is % difference in reflectance (washing power),
$R_g$ is % reflectance of the washed fabric
$R_u$ is % reflectance of the unwashed fabric.
*Eidgenössische Materialprüfanstalt The deposit on the fabric (incrustation) was determined in the form of inorganic fabric ash as the ignition residue in percent at 800° C.

Some of the detergent powders were prepared by the so-called hot-spraying process and the others by the so-called spray mist mixing process (dry mixing process). Hot-spraying was carried out by means of a laboratory spray dryer (Büchi, type 190) with an inlet temperature of about 180° C., an outlet temperature of about 100° C., a spraying pressure of 5 bar and a solids concentration of 30% by weight.

In the spray mist mixing process, a free-falling mixer was used, in which the liquid components were sprayed onto the pulverulent dry components by means of a suitable spraying device. The procedure is described in detail in "Seifen, Fette, Öle, Wachse", 99, (1973), 351–357.

Detergent formations and washing tests are described in the tables below.

| Detergent formulations | Spray mist mixing tests Example | |
|---|---|---|
| | Comparison | 4 |
| Saccharose tricarboxylic acid (STA) (known product as described in German Offenlegungsschrift 3,535,720) | 10.0 | — |
| Ether carboxylic acid according to the invention (as Example 1) | — | 10.0 |
| Zeolite | 21.5 | 21.5 |
| Sodium perborate tetrahydrate | 20.0 | 20.0 |
| Anionic surfactants (alkylbenzenesulfonate) | 7.0 | 7.0 |
| Nonionic surfactants (alkoxylated alcohols) | 4.0 | 4.0 |
| Soaps | 3.5 | 3.5 |
| Sodium silicate | 5.0 | 5.0 |
| Carboxymethylcellulose | 1.0 | 1.0 |
| Methylcellulose | 0.5 | 0.5 |
| | Balance to 100% customary detergent components | |

| Washing test according to DIN 44983 (two-liquor process, laundry of 60° C., water hardness 18° German hardness) | | | | |
|---|---|---|---|---|
| | Dosage (g) prewash/ | Primary washing effect of various test fabrics (% difference in reflectance) | | |
| Example | clear wash | EMPA cotton No. 101 | WFK cotton No. 10C | WFK cotton No. 10D |
| Comparison | 150/150 | 26 | 21 | 23 |
| 4 | 150/150 | 31 | 27 | 30 |

| Washing test according to DIN 44983 (two-liquor process, laundry of 90° C., water hardness 18° German hardness) | | | | |
|---|---|---|---|---|
| | Dosage (g) prewash/ | % ash after 25 wash cycles | | |
| Example | clear wash | Terry | Cotton (EMPA) | Double-rib (WFK) |
| Comparison | 150/150 | 2.1 | 2.3 | 2.4 |
| 4 | 150/150 | 0.9 | 0.4 | 0.4 |

We claim:

1. A process for the preparation of ether carboxylic acids by alkoxylation of carbohydrates and derivatives thereof, followed by oxidation, which comprises either ethoxylating the carbohydrate or derivatives thereof directly in the usual manner or first alkoxylating them using a higher alkylene oxide and then ethoxylating them and oxidizing the aqueous solution thus obtained without any further treatment in a pH range in which the carbohydrates and carboxylic acids derived therefrom are stable, using oxygen as the oxidizing agent in the presence of a catalyst containing at least one platinum metal.

2. The process as claimed in claim 1, wherein the amount of the higher alkylene oxide is up to 3 mol and that of the ethylene oxide is from 1 to 10 mol, in each case relative to 1 mol of OH in the carbohydrate and the derivative thereof.

3. The process as claimed in claim 1 wherein the catalyst contains either a combination of palladium and platinum or only platinum as the platinum metal.

4. The process as claimed in claim 1 wherein the catalyst comprises 1 to 15% by weight, of the platinum metal and a support, preferably activated carbon.

5. The process as claimed in claim 1 wherein the oxidation is carried out in a pressure range from 0.5 to 100 bar.

6. The process as claimed in claim 1 wherein the aqueous solution contains a solubilizing agent which is inert under the reaction conditions.

7. The process as claimed in claim 1 wherein the oxidation is carried at a temperature from 5° to 80° C.

8. The process as claimed in claim 1 wherein the oxidation is carried out at a pH from 5 to 9.

9. A method for using the ether carboxylic acids obtained by he process as claimed in claim 1, comprising the step of introducing a said ether carboxylic acid into a detergent or cleaning agent formulation as a builder therefor.

10. A detergent or cleaning agent, which contains the ether carboxylic acids prepared as claimed in claim 1.

11. The process as claimed in claim 2, wherein the total amount of alkylene oxide is up to 5 mol.

12. The process as claimed in claim 4, wherein the catalyst comprises 5 to 10% by weight of the platinum metal and an activated carbon support.

13. The process as claimed in claim 5, wherein the oxidation is carried out in a pressure range from atmospheric pressure to 10 bar.

14. The process as claimed in claim 6, wherein said solubilizing agent is present in an amount of 10 to 75% by weight, said solubilizing agent being a glycol ether without hydroxyl groups.

15. The process as claimed in claim 7, wherein the oxidation is carried out a temperature from 10 to 60°.

16. The process as claimed in claim 8, wherein the oxidation is carried out at a pH from 6 to 8.5.

* * * * *

UNITED STATES PATENT AND TRADEMARK OFFICE
CERTIFICATE OF CORRECTION

PATENT NO.: 5,223,642

DATED: June 29, 1993

INVENTOR(S): Karl-Heinz Schönwälder, Ernst Ingo Leupold, Werner Gohla, Franz-Josef Dany and Merten Schlingmann

It is certified that error appears in the above-identified patent and that said Letters Patent is hereby corrected as shown below:

On the title page, item [75], the list of inventors should read:

Karl-Heinz Schönwälder, Kelkheim/Taunus;

Ernst Ingo Leupold, Neu-Anspach;

Werner Gohla, Niederkassel;

Franz-Josef Dany, Erftstadt;

Merten Schlingmann, Königstein; all of Fed. Rep. of Germany.

At column 4, line 27 "209" should read --20 g--.

At column 4, line 61 "Preparation" should read --Application--.

In claim 4, at column 6, line 35, delete the "," and at column 6, line 36, delete ", preferably activated carbon".

In claim 7, at column 6, line 43, insert --out-- after "carried".

UNITED STATES PATENT AND TRADEMARK OFFICE
CERTIFICATE OF CORRECTION

PATENT NO. : 5,223,642

DATED : June 29, 1993

INVENTOR(S) : Karl-Heinz Schönwälder, Ernst Ingo Leupold, Werner Gohla, Franz-Josef Dany and Merten Schlingmann It is certified that error appears in the above-indentified patent and that said Letters Patent is hereby corrected as shown below:

In claim 7, at column 6, line 43, insert --out--after "carried".

Signed and Sealed this

Eighth Day of March, 1994

Attest:

BRUCE LEHMAN

Attesting Officer

Commissioner of Patents and Trademarks